(12) United States Patent
Kim et al.

(10) Patent No.: US 9,819,842 B2
(45) Date of Patent: Nov. 14, 2017

(54) REMOTE INSPECTION APPARATUS FOR HEATING TUBE OF STEAM GENERATOR

(71) Applicant: KOREA PLANT SERVICE & ENGINEERING CO., LTD, Naju-si, Jeollanam-do (KR)

(72) Inventors: Kyung sub Kim, Suwon-si (KR); Jang Myong Woo, Yongin-si (KR); Sung Ho Park, Yongin-si (KR); Hong Seok Ryu, Yongin-si (KR)

(73) Assignee: KOREA PLANT SERVICE & ENGINEERING CO., LTD, Naju-si (KR)

( * ) Notice: Subject to any disclaimer, the term of this patent is extended or adjusted under 35 U.S.C. 154(b) by 226 days.

(21) Appl. No.: 14/667,020

(22) Filed: Mar. 24, 2015

(65) Prior Publication Data

US 2015/0271366 A1   Sep. 24, 2015

(30) Foreign Application Priority Data

Mar. 24, 2014 (KR) .................. 10-2014-0033806

(51) Int. Cl.
| | |
|---|---|
| H04N 7/18 | (2006.01) |
| H04N 5/225 | (2006.01) |
| F22B 37/00 | (2006.01) |
| G01N 21/954 | (2006.01) |
| F27D 21/02 | (2006.01) |

(52) U.S. Cl.
CPC ............ *H04N 5/225* (2013.01); *F22B 37/005* (2013.01); *G01N 21/954* (2013.01); *F27D 2021/026* (2013.01); *H04N 2005/2255* (2013.01)

(58) Field of Classification Search
CPC .................................................. F27D 2021/026
See application file for complete search history.

(56) References Cited

FOREIGN PATENT DOCUMENTS

JP      10-1086344 B1    11/2011

OTHER PUBLICATIONS

Korean Office Action for KR 102014-0033806 dated Jul. 9, 2014.

*Primary Examiner* — Young Lee
(74) *Attorney, Agent, or Firm* — Sughrue Mion, PLLC

(57) ABSTRACT

Provided herein is a remote inspection apparatus for a heating tube of a steam generator, the apparatus including a fixing unit installed in a flange surface of a hand hole of the steam generator in a fixed manner, and having one or more rail guiders for guiding a guide rail into the steam generator; the guide rail configured to be guided by the rail guider to enter between the heating tube and a divider plate inside the steam generator; a rail driving unit fitted at one end of the guide rail and arranged outside the steam generator, and having a bobbin around which a steel belt is wound; and a probe feeding unit configured to receive a driving force from the rail driving unit through the steel belt to be moved along the guide rail, and having a band shaped probe extending in a length direction and an inspection camera fitted at one end of the probe.

14 Claims, 17 Drawing Sheets

REMOTE INSPECTION APPARATUS FOR HEATING TUBE OF STEAM GENERATOR

CROSS-REFERENCE TO RELATED APPLICATION

The present application claims priority to Korean patent application number 10-2014-0033806, filed on Mar. 24, 2014, the entire disclosure of which is incorporated herein in its entirety by reference.

BACKGROUND

Field of Invention

Various embodiments of the present disclosure relate to a remote inspection apparatus for a heating tube of a steam generator, and more particularly to a remote inspection apparatus for a heating tube of a steam generator capable of approaching inside the steam generator through a hand hole of the steam generator and inspecting a deposited state of foreign substance or sludge introduced into an exterior of the heating tube or into a gap between the heating tubes.

Description of Related Art

Generally, using a steam generator, a nuclear power plant generates the steam needed to produce electricity from a steam turbine and generator. In such a steam generator, a plurality of heating tubes may be arranged in bundles, each heating tube exchanging heat between primary water that includes radioactive material and secondary water that drives a turbine, and separating the primary water and secondary water from each other.

In a steam generating process, the primary water heated while passing through a reactor flows inside the heating tube of the steam generator while the secondary water is supplied to the exterior of the heating tube, and then the primary water and secondary water exchange heat through the wall of the heating tube. Then, the heat-exchanged primary water is circulated back to the reactor along a conduit of a closed circuit while the secondary water is converted into steam.

In the steam generator, since the primary and secondary water exchange heat through the wall of the heating tube, high temperature and high pressure radioactive water (primary water) flows inside the heating tube while nonradioactive water (secondary water) flows outside the heating tube. Therefore, in a case the heating tube is damaged, the radioactive water (primary water) inside the heating tube may leak outside the heating tube and mix with the nonradioactive water (secondary water), which may result in a serious problem of contaminating the entire area to which the steam converted from the nonradioactive water (secondary water) is supplied. Therefore, securing the integrity of the heating tube is dealt as the most important task in operating a nuclear power plant.

Hereinafter, the aforementioned steam generator will be explained in further detail with reference to the attached drawings.

FIG. 1 is a schematic cross-sectional view of an interior of a steam generator, and FIG. 2 is a schematic view illustrating an operational principle of the steam generator of FIG. 2.

Referring to FIGS. 1 and 2, the steam generator 10 may consist of an inlet nozzle 11 through which a primary reactor coolant enters, heating tubes 13 where heat exchange is conducted, and an outlet nozzle 12 that transmits the heat from the reactor coolant entering the inlet nozzle 11 to a secondary coolant. The heating tubes 13 are placed on top of a tube sheet 14, and the heating tubes 13 being supported by tube support plates 15 at every certain vertical height thereof. Between the tube support plate 15 and the tube sheet, a flow distributing plate 16 on a donut shaped plate is placed to support the heating tube 13. The plurality of tube support plates 15 spaced by a certain vertical distance that support the heating tube 13 and the heating tube 13 combines a wrapper 18 having an open lower part and a steam outlet 17 on its top end, the wrapper 18 playing the role of receiving water downwards along an inner wall of an external housing 19, and discharging upwards the steam generated from the supplied water by the heating tube 13.

In the steam generator 10, the primary reactor coolant enters the inlet nozzle 11, flows inside the plurality of heating tubes 13, passes through the outlet nozzle 12, thereby transmitting the heat to the secondary coolant outside, wherein steam is generated. In such a steam generator 10, the part where the reactor coolant flows is referred to as a primary side, and the part where the supplied water and steam flow is referred to as a secondary side. The secondary water may consist of main vapor water, turbine water, condensed water, and supplied water. The vapor generated at the secondary side of the steam generator 10 moves along a main vapor tube, thereby rotating the turbine.

Supply of the secondary water to the secondary side to generate steam in such a steam generator 10 is made through filtration and chemical treatment, but the secondary water is introduced into the steam generator 10 together with foreign substance and sludge generated through various routes while circulating inside the conduit, and is thus deposited on the tube sheet 14, tube support plate 15, and flow distributing plate 16, or stick to an outer wall of the heating tube 13, thereby deteriorating or damaging the heating effect. That is, the steam generator 10 is arranged as thousands of heating tubes 13 form bundles, and thus foreign substance or impurities introduced through various routes or generated as an operating fluid passes through may be deposited on the exterior surface of the heating tubes 13, which may not only deteriorate the heat exchanging capacity of the heating tubes 13 but also the foreign substance and impurities solidified as sludge may cause denting between the tube support plate 15 and heating tubes 13, damaging the heating tubes 13.

Therefore, removing scale from the surface of the heating tubes 13 and the sludge from the tube support plate 15 is becoming an essential means for securing the integrity of the heating tubes 13 and the efficiency of the steam generator. And for this purpose, various inspection facilities such as small endoscope cameras are being adopted to check the state of the flow distributing plate 16, heating tubes 13 and tune sheet 14.

For example, there is a well known visual inspection apparatus (so called, KIIS) developed by the applicant for inspecting gaps of heating tubes of steam generators. Such a visual inspection apparatus is configured to be inserted through a hand hole placed in a lower part of the steam generator. The visual inspection apparatus enters in a direction perpendicular to a divide plate as it moves along a circumferential direction using a space between the heating tube bundles and shroud, and a probe is inserted between the tubes to perform an inspection. However, in such a visual inspection apparatus, sagging may occur as a robot moves, due to gravity, and thus the apparatus requires constant correctional control, and not only that, it would take a long time to do the setting and to correct errors before moving along columns of the heating tubes and conducting the inspection, thereby deteriorating the operational efficiency.

PRIOR TECHNOLOGY DOCUMENTS

Patent Document (Patent document 1) Korean Patent Registration no. 10-1086344 (registered on Nov. 17, 2011)

SUMMARY

Various embodiments of the present disclosure provides a remote inspection apparatus for a heating tube of a steam generator capable of approaching inside the steam generator through a hand hole of the steam generator and of inspecting a wide area to detect a deposited state of foreign substance or sludge introduced into an exterior of the heating tube or into a gap between the heating tube, at a rapid speed and high operating efficiency.

An embodiment of the present disclosure provides a remote inspection apparatus for a heating tube of a steam generator, the apparatus including a fixing unit installed in a flange surface of a hand hole of the steam generator in a fixed manner, and having one or more rail guiders for guiding a guide rail into the steam generator; the guide rail configured to be guided by the rail guider to enter between the heating tube and a divider plate inside the steam generator; a rail driving unit fitted at one end of the guide rail and arranged outside the steam generator, and having a bobbin where a steel belt is wound; and a probe feeding unit configured to receive a driving force from the rail driving unit through the steel belt to be moved along the guide rail, and having a band shaped probe extending along a length direction, and an inspection camera fitted at one end of the probe.

A remote inspection apparatus for a heating tube of a steam generator according to various embodiments of the present disclosure may be easily installed through a hand hole of the steam generator, may easily approach even an area where a conventional inspection apparatus could not easily reach, and may thus contribute to thoroughly inspecting the steam generator or heating tubes and securing integrity thereof.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

DETAILED DESCRIPTION

Figure 1:
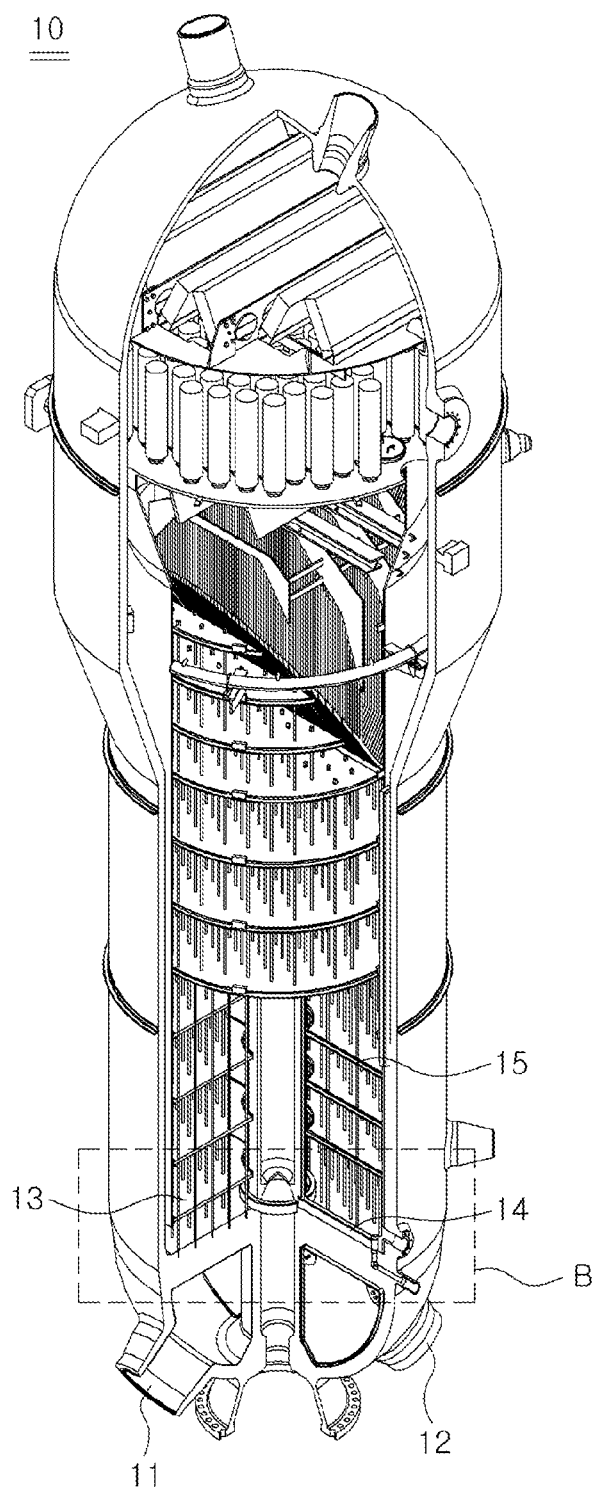
FIG. 1 is a schematic cross-sectional view of an interior of a steam generator.

Hereinafter, embodiments will be described in greater detail with reference to the accompanying drawings. Embodiments are described herein with reference to cross-sectional illustrations that are schematic illustrations of embodiments (and intermediate structures). As such, variations from the shapes of the illustrations as a result, for example, of manufacturing techniques and/or tolerances, are to be expected. Thus, embodiments should not be construed as limited to the particular shapes of regions illustrated herein but may include deviations in shapes that result, for example, from manufacturing. In the drawings, lengths and sizes of layers and regions may be exaggerated for clarity. Like reference numerals in the drawings denote like elements.

Terms such as 'first' and 'second' may be used to describe various components, but they should not limit the various components. Those terms are only used for the purpose of differentiating a component from other components. For example, a first component may be referred to as a second component, and a second component may be referred to as a first component and so forth without departing from the spirit and scope of the present disclosure. Furthermore, 'and/or' may include any one of or a combination of the components mentioned.

Furthermore, a singular form may include a plural from as long as it is not specifically mentioned in a sentence. Furthermore, "include/comprise" or "including/comprising" used in the specification represents that one or more components, steps, operations, and elements exist or are added.

Furthermore, unless defined otherwise, all the terms used in this specification including technical and scientific terms have the same meanings as would be generally understood by those skilled in the related art. The terms defined in generally used dictionaries should be construed as having the same meanings as would be construed in the context of the related art, and unless clearly defined otherwise in this specification, should not be construed as having idealistic or overly formal meanings.

It is also noted that in this specification, "connected/coupled" refers to one component not only directly coupling another component but also indirectly coupling another component through an intermediate component. On the other hand, "directly connected/directly coupled" refers to one component directly coupling another component without an intermediate component.

Figure 3:
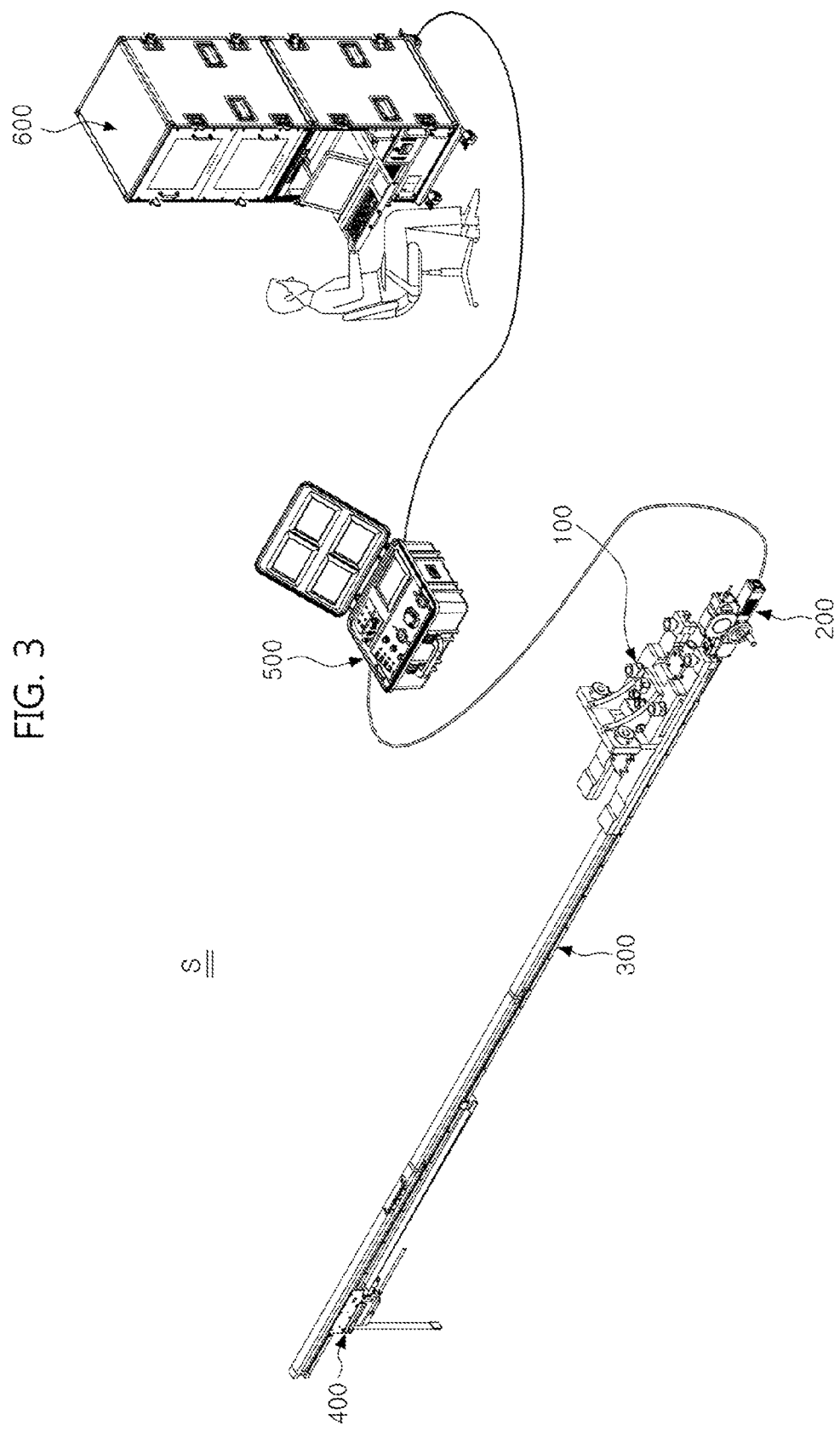
FIG. 3 is an overall view illustrating a remote inspection apparatus for a heating tube of a steam generator according to an embodiment of the present disclosure.

FIG. 3 is an overall view illustrating a remote inspection apparatus for a heating tube of a steam generator according to an embodiment of the present disclosure.

Referring to FIG. 3, the remote inspection apparatus for a heating tube of a steam generator according to the embodiment of the present disclosure (hereinafter referred to as 'remote inspection apparatus S') is configured for the purpose to approach inside the steam generator using an empty space between a divider plate at a lower end of the steam generator and heating tube bundles, and to inspect foreign substance. The remote inspection apparatus may include a fixing unit 100 fixed to a flange surface of a hand hole of the steam generator, a guide rail 300 guided by the fixing unit 100 to extend inside the steam generator, a probe feeding unit 400 configured to move along the guide rail 300 and inspect foreign substance in a gap between heating tubes, and a rail driving unit 200 fitted to one end of the guide rail 300 to move the probe feeding unit 400.

Furthermore, the remote inspection apparatus S according to the embodiment of the present disclosure may include a local control unit 500 for monitoring from outside the steam generator and for setting an initial position or setting a posture and so forth, and a remote control unit 600 for various drive controls or for collecting inspection data from outside a reactor.

In the remote inspection apparatus S according to embodiment of the present disclosure, the fixing unit 100 is installed in a fixed manner to a flange surface of each hand hole arranged in a lower part of the steam generator distanced by 180 degrees from one another, the guide rail 300 is entered between the divider plate and the heating tube bundles under the guidance of the fixing unit 100, the probe feeding unit 400 that is movable along the guide rail 300 is moved to a set position by the rail driving unit 200, and then the probe is inserted into a gap between the heating tubes so as to inspect a state of sludge or deposition of foreign substance inside or outside the heating tubes. In such a process, the local control unit 500 performs driving control necessary for monitoring installing process or for setting an initial position or posture during the installing process, and the remote control unit 600 analyzes inspection data collected by the probe and performs various driving controls necessary for the inspection.

Figure 4:
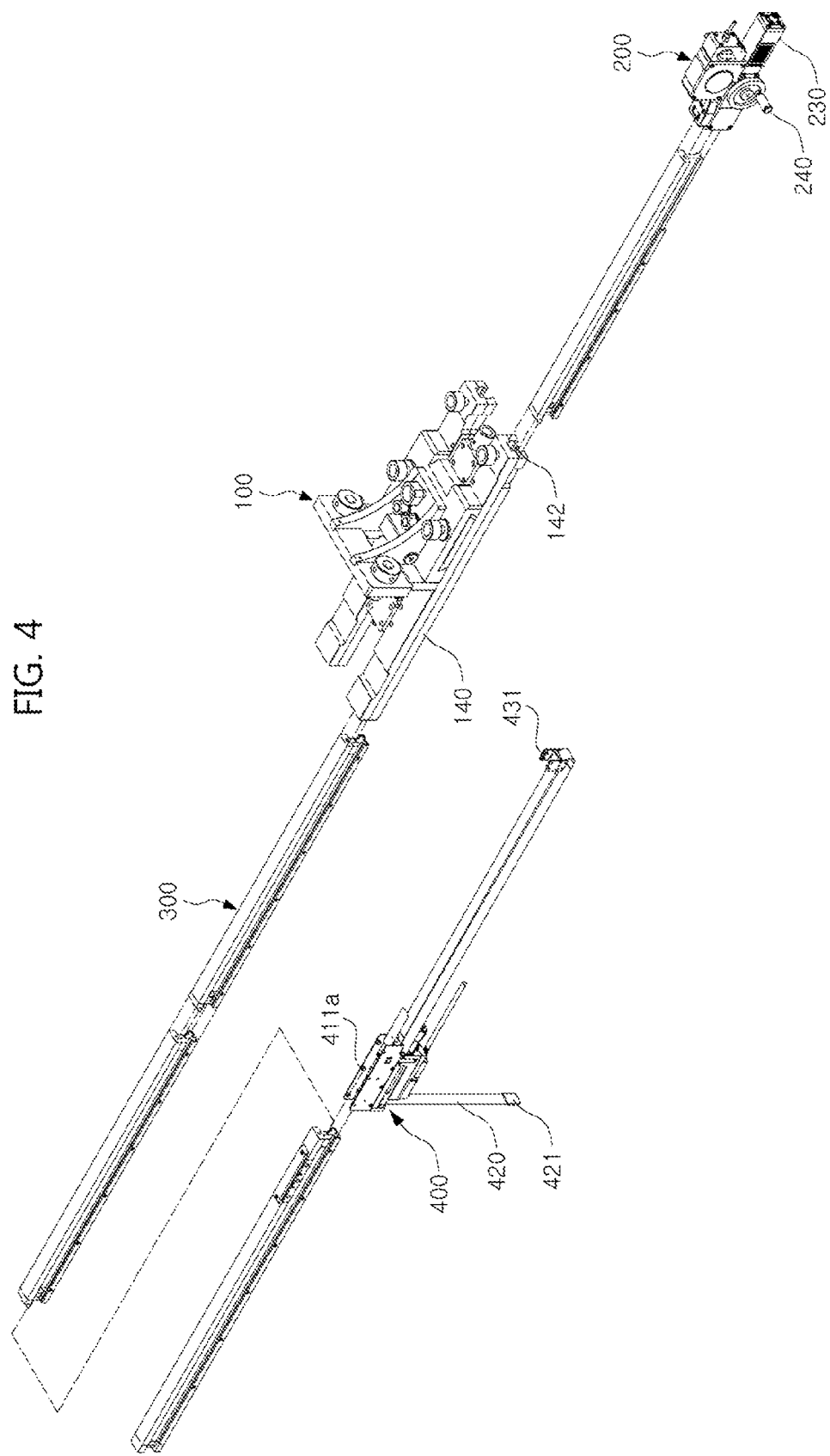
FIG. 4 is a perspective view illustrating a fixing unit, guide rail, probe feeding unit and rail driving unit illustrated in FIG. 3.

FIG. 4 is a perspective view illustrating a fixing unit, guide rail, probe feeding unit and rail driving unit illustrated in FIG. 3.

Referring to FIG. 4, the fixing unit 100 that is fixed to the flange surface of the hand hole of the steam generator may have one or more rail guiders 140 in its lower part. The rail guider 140 may have, on its lower surface, a rail guiding groove 142 where the guide rail 300 is fitted, and the present embodiment exemplifies a case where a rail guider 140 is arranged in a left and right side of the fixing unit 100, that is, where there are a total of two rail guiders 140.

Furthermore, the guide rail 300 is inserted or fitted into the rail guiding groove 142 of the rail guider 140 so that its entering into the steam generator may be guided. A plurality of guide rails 300 may be separately formed when necessary. In the present embodiment, a total of four guide rails 300 are separately formed along a length direction. However, the number of guide rails 300 may of course vary depending on the size of the steam generator or necessary inspection setting positions.

Meanwhile, at one end of the guide rail 300, the rail driving unit 200 may be fitted to allow movement of the probe feeding unit 400. In the present embodiment, there are four guide rails 300 separately formed along the length direction, in which case the rail driving unit 200 may be mounted at one end of the guide rail 300 arranged in a rightmost end in the drawings. The rail driving unit 200 is configured to transmit a driving force to allow movement of the probe feeding unit 400 through a steel belt. The rail driving unit 200 may also have a driving motor 230 or handle unit 240, and may be configured to control the movement of the probe feeding unit 400 automatically or manually when necessary.

The probe feeding unit 400 may include a probe 420 configured to enter a gap between the heating tubes so as to inspect foreign substance or sludge. And at one end of such a probe 420, an inspection camera 421 is fitted so as to check in real time a state of an interior or exterior of the heating tubes or collect image data necessary for the inspection. Furthermore, the probe feeding unit 400 may be moved up to an inspecting position along the guide rail 300 by a control of the rail driving unit 200. For this purpose, at a housing top end of the probe feeding unit 400 or at a top end of a trolley that supports the probe, a roller 411a, 431 configured to conduct a rolling motion along the guide rail 300 may be provided.

Figure 5:
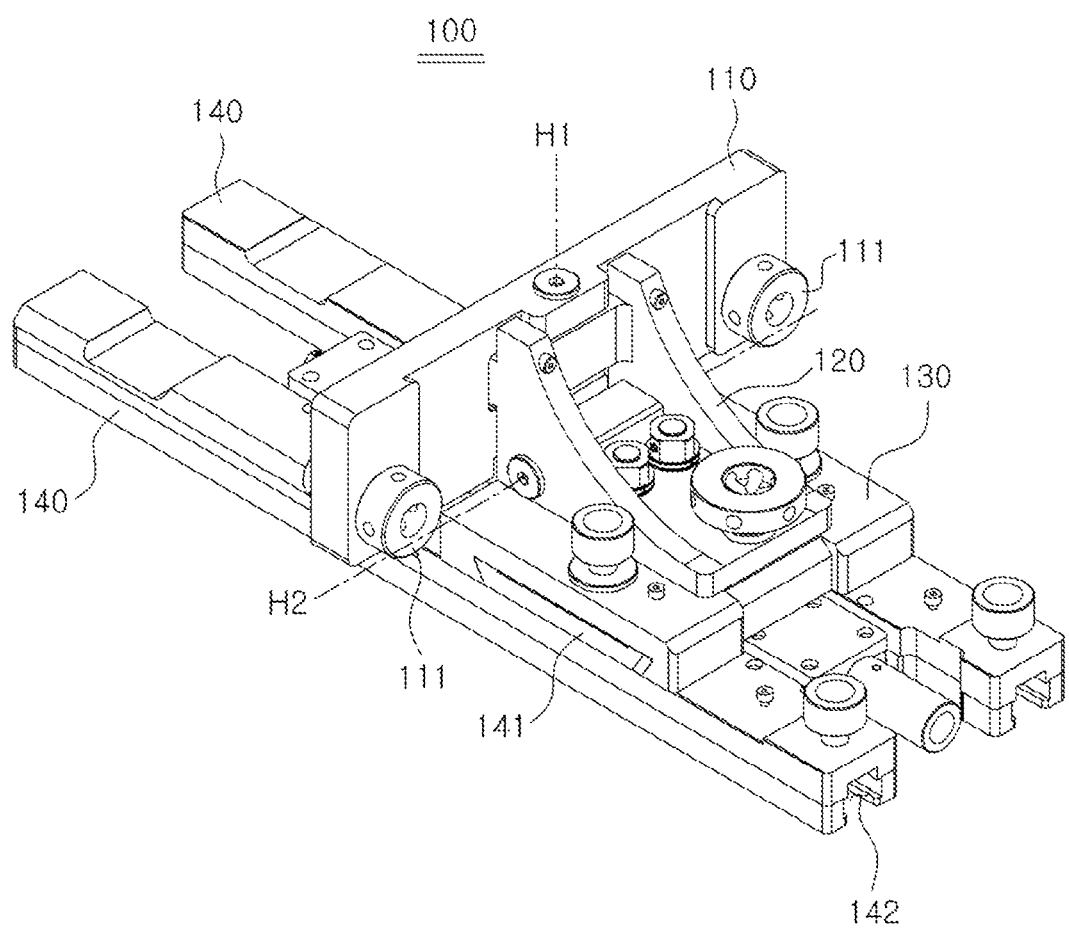
FIG. 5 is an enlarged perspective view of the fixing unit illustrated in FIG. 3.
Figure 6:
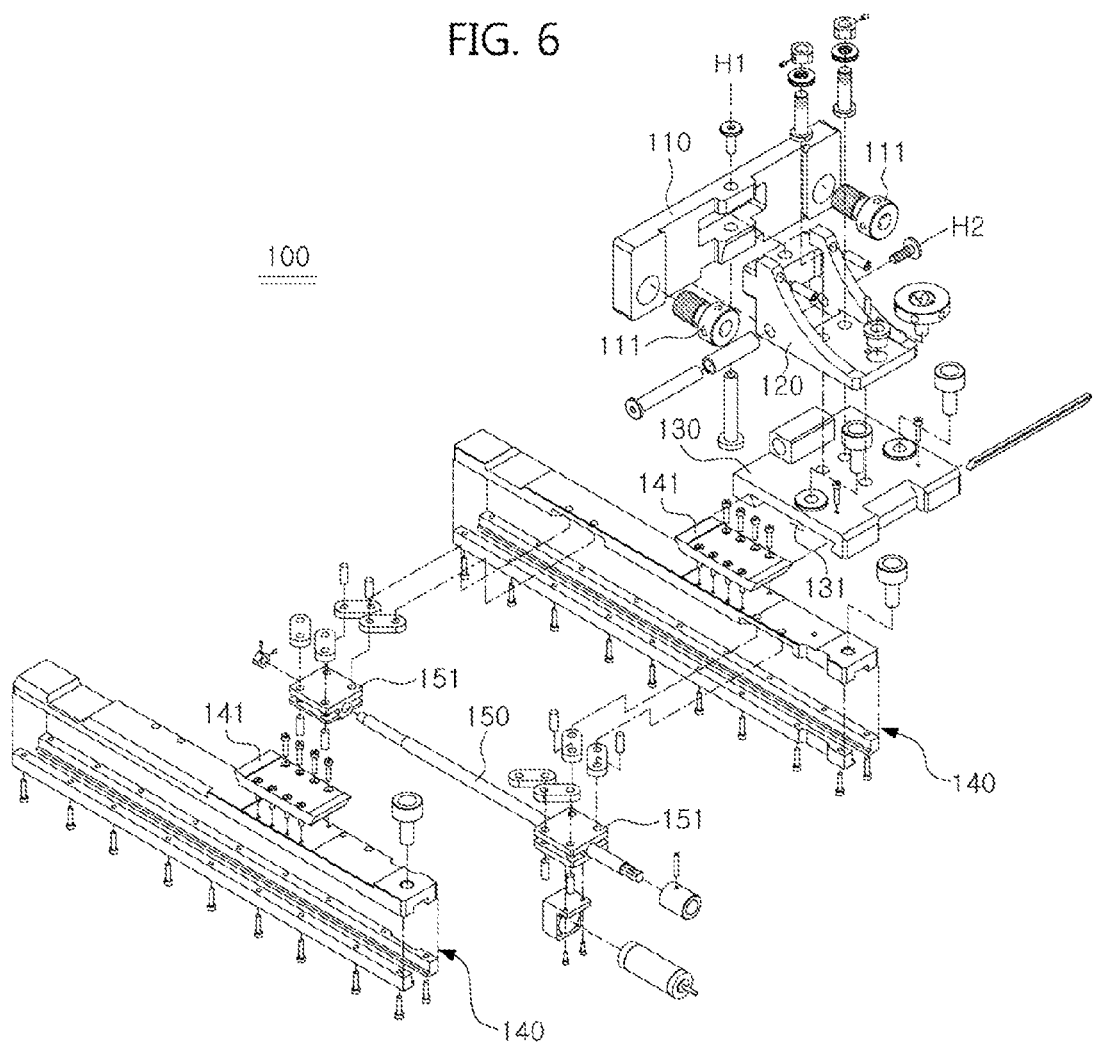
FIG. 6 is an exploded perspective view of the fixing unit illustrated in FIG. 5.

FIG. 5 is an enlarged perspective view of the fixing unit illustrated in FIG. 3. FIG. 6 is an exploded perspective view of the fixing unit illustrated in FIG. 5.

Referring to FIG. 5 and FIG. 6, the fixing unit 100 may have a fixing block 110 configured to be attached to the flange surface of the hand hole of the steam generator. The fixing block 110 may be formed to have a roughly square plate shape, and may be bolt-attached to the flange surface of the band hole by one or more fixing bolts 111.

Furthermore, the fixing unit 100 may have a hinge block 120 configured to be secured to the fixing block 110 in a rotatable manner. The hinge block 120 may be attached to the fixing block 110 such that it is rotatable with respect to the fixing block 110 around a first hinge axis (H1) having an up-down direction. Such a hinge block 120 allows the fixing unit 100 to control the rail guider 140 to rotate by a predetermined extent around the up-down axis, whereby a position and direction of the guide rail 300 guided by the rail guider 140 may be adjusted. Hereinafter, such rotation made around the up-down direction axis will be referred to as 'rolling' for convenience of explanation. In other words, the hinge block 120 is enabled to rolling-adjust the rail guider 140 or the guide rail 300 guided by the rail guider 140.

Meanwhile, the fixing unit 100 may have a sliding block 130 secured to the hinge block 120 in a rotatable manner. The sliding block 130 may be attached to the hinge block 120 such that it is rotatable with respect to the hinge block 120 around a second hinge axis (H2) having a width direction. Such a sliding block 130 allows the fixing unit 100 to adjust the rail guider 140 or guide rail 300 in a rotatable manner around the width direction axis. Especially, rotation of the sliding block 130 enables tilting adjustment for compensating sagging of the guide rail 300 extending in a length direction. Hereinafter, rotation made around the width direction axis will be referred to as 'tilting' for convenience of explanation.

Furthermore, the sliding block 130 may have a sliding groove 131 on its lower surface. The sliding groove 131 may be formed to have a reversed trapezoidal shape extending from one end of the lower surface of the sliding block 130 to an opposite side in a width direction. Such a sliding groove 131 may be secured to a mounting block 141 of the rail guider 140 that will be explained hereinafter, and as the mounting block 141 is moved left or right in the sliding groove 131, a position or distance of the rail guider 140 may be controlled in a width direction.

Meanwhile, the fixing unit 100 may have one or more rail guiders 140 configured to be secured to the sliding block 130. The rail guider 140 is for guiding the guide rail 300 to enter the steam generator, and the rail guider 140 may have a rail guiding groove 142 configured to be secured to the guide rail 300, and may extend by a predetermined extend in the length direction. As aforementioned, a direction or position of such a rail guider 140 may be finely adjusted by the rolling or tilting of the hinge block 120 or sliding block 130.

Furthermore, the rail guider 140 may be fitted to the sliding groove 131 of the lower surface of the sliding block 130 by the mounting block 141 and its position may be adjusted by a predetermined extent in a width direction. That is, on an upper surface of the rail guider 140, the mounting block 141 having a shape corresponding to that of the sliding groove 131 may be provided, and the rail guider 140 may be fitted to and supported by the sliding block 130 as the mounting block 141 is fitted to the sliding groove 131. Therefore, a left or right movement or position of the rail guider 140 may be adjusted as the mounting block 141 is moved left or right inside the sliding groove 131, and when there are two rail guiders 140 as in the present embodiment, a distance between the two rail guiders 140 may be adjusted by the mounting block 141 as well.

Moreover, when necessary, the fixing unit 100 may have a distance adjusting bar 150 configured to adjust the distance between two rail guiders 140. Such a distance adjusting bar 150 may be hinge attached to each of the left and right rail guiders 140 as a hinge bracket 151 provided at each of both sides of the distance adjusting bar 150 is hinge-attached to the left and right rail guiders 140 through a plurality of hinge pieces (not illustrated). Such a distance adjusting bar 150 allows the distance between the left and right rail guiders 140 to be adjusted more easily as it is moved front and back along the length direction.

Figure 7:
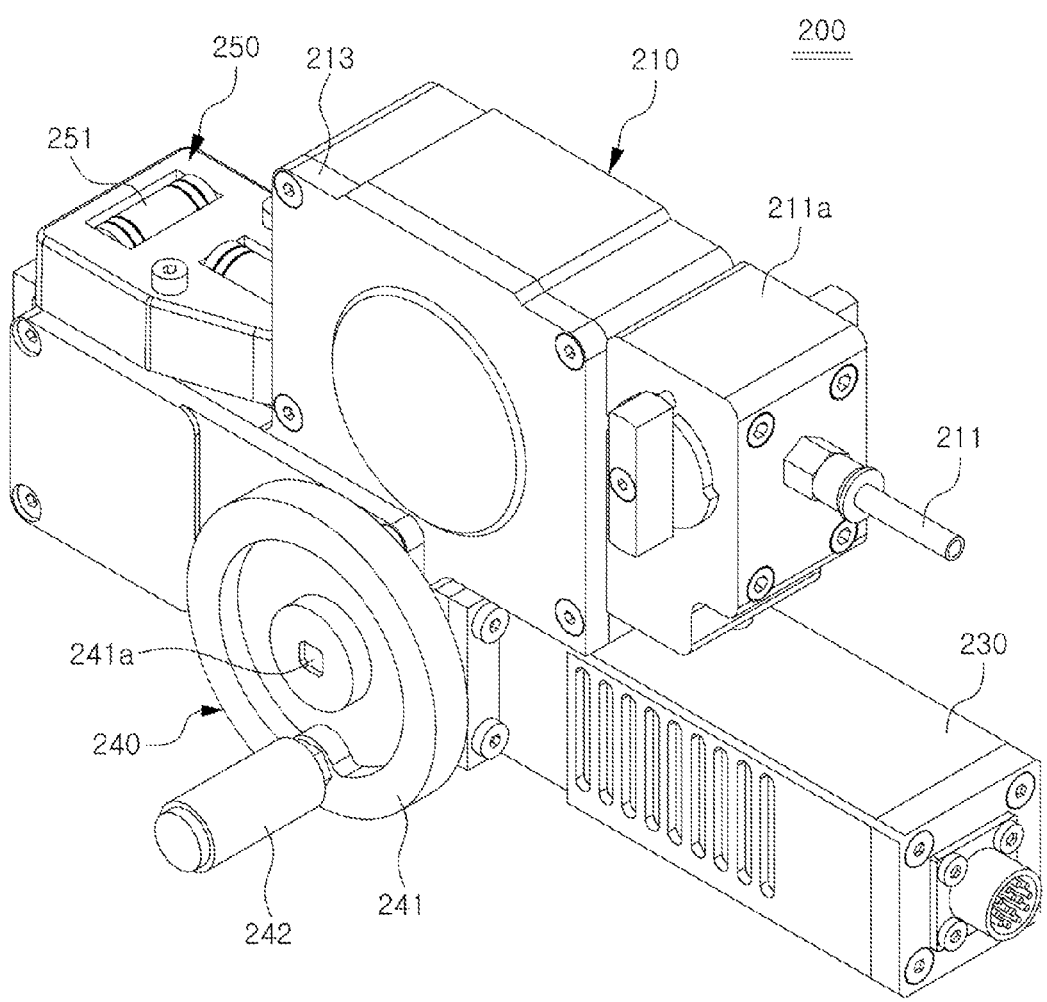
FIG. 7 is an enlarged perspective view of the rail driving unit illustrated in FIG. 3.
Figure 8:
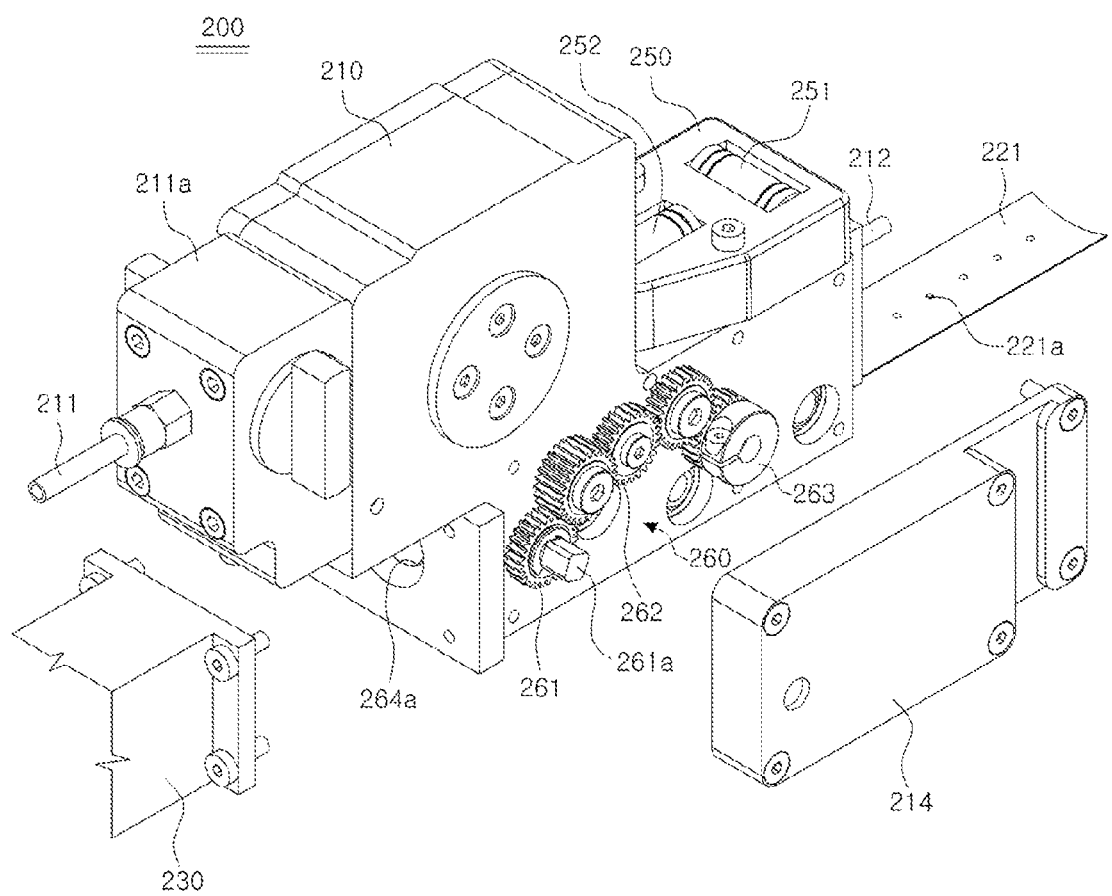
FIG. 8 is an exploded perspective view of the rail driving unit illustrated in FIG. 7 with a right cover separated from the rail driving unit.
Figure 9:
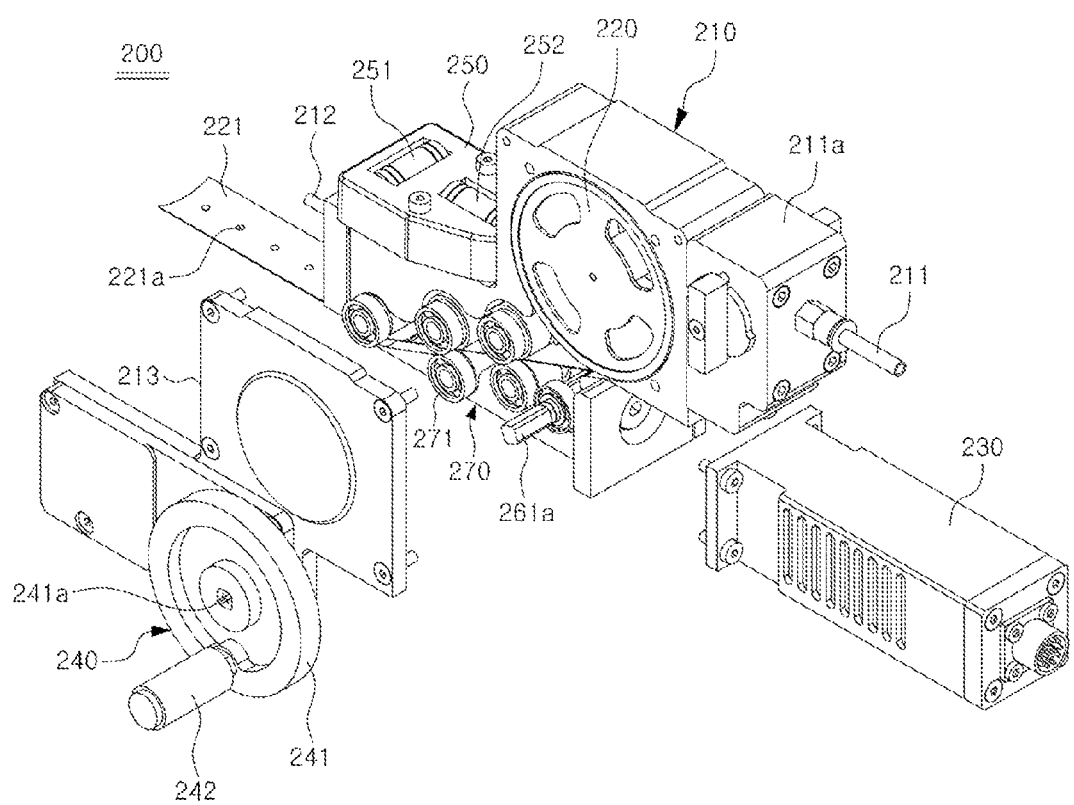
FIG. 9 is an exploded perspective view of the rail driving unit illustrated in FIG. 7 with a left cover separated from the rail driving unit.
Figure 10:
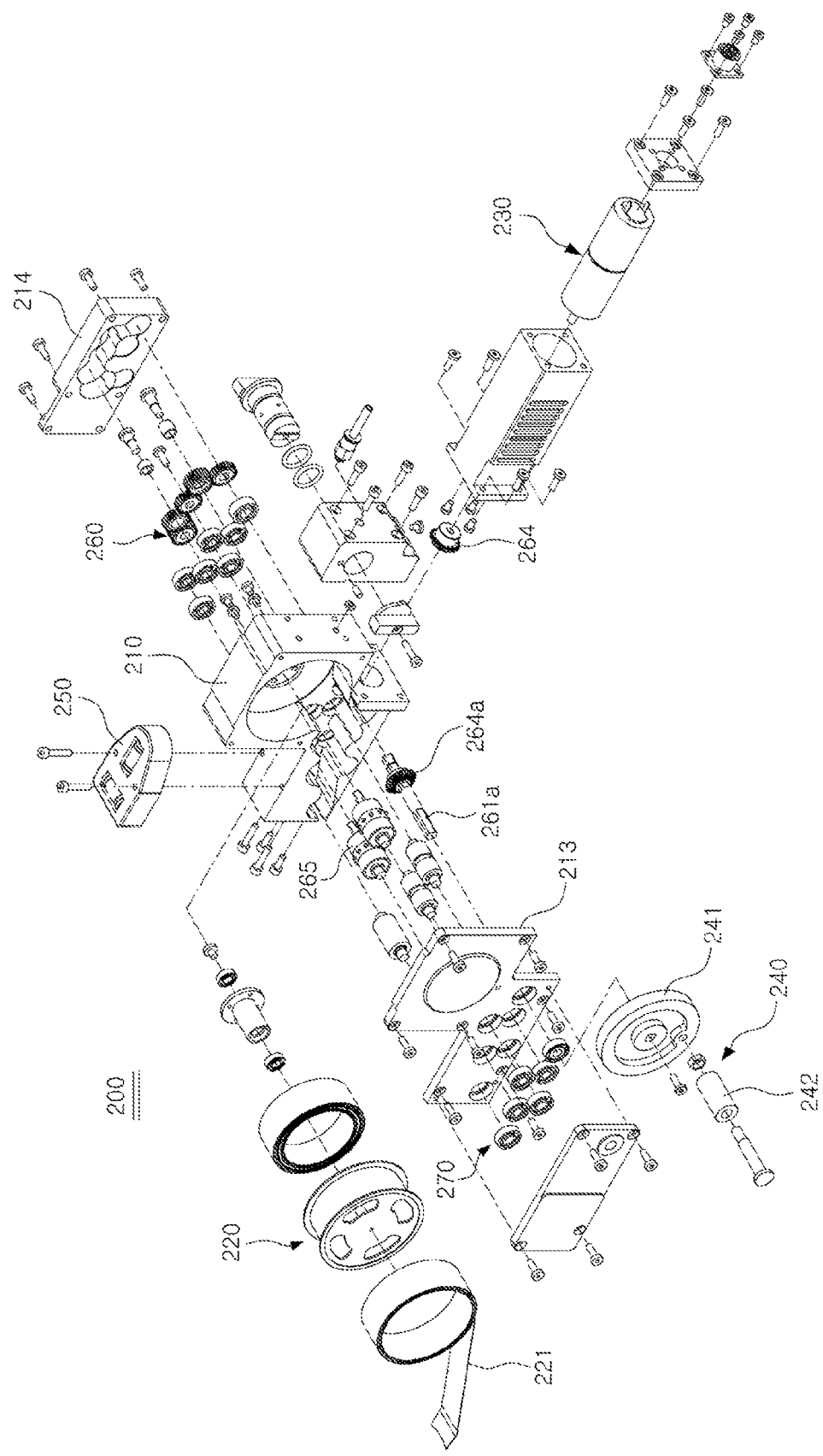
FIG. 10 is an exploded perspective view of the rail driving unit illustrated in FIG. 7.

FIG. 7 is an enlarged perspective view of the rail driving unit illustrated in FIG. 3. FIG. 8 is an exploded perspective view of the rail driving unit illustrated in FIG. 7 with a right cover separated from the rail driving unit. FIG. 9 is an exploded perspective view of the rail driving unit illustrated in FIG. 7 with a left cover separated from the rail driving unit. FIG. 10 is an exploded perspective view of the rail driving unit illustrated in FIG. 7.

Referring to FIGS. 7 to 10, the rail driving unit 200 may have a housing 200. The housing 200 forms an overall exterior appearance of the rail driving unit 200, and provides a space where a bobbin 220 that will be explained hereinafter may be fitted. A left and right surface of the housing 200 may each be covered by a cover 213, 214, respectively. For convenience of explanation, these covers will be referred to as a left cover 213 and right cover 214. It is to be noted that FIG. 8 illustrates a right surface of the housing 200 with the right cover 214 separated from the housing 200, whereas FIG. 9 illustrates a left surface of the housing 200 with the left cover 213 separated from the housing 200.

Meanwhile, the rail driving unit 200 may have a bobbin 220 where a steel belt 221 is wounded. The bobbin 220 may be assembled inside the housing 200, and may have the steel belt 221 for moving the probe feeding unit 400. The steel belt 221 may be kept wound around the bobbin in a rolled up manner, and be unwound by a handing unit 240 or driving motor 230 that will be explained hereinafter and be provided towards the probe feeding unit 400. This will be explained in further detail hereinafter.

Furthermore, the rail driving unit 200 may have the driving motor 230 configured to provide the steel belt 221 wound around the bobbin 220 to the probe feeding unit 400 to move the probe feeding unit 400. The driving motor 230 may be fitted to one side of the housing 200, and a driving force may be transmitted to the steel belt 221 through a gear set 260 to unwind the steel belt 221 from the bobbin 220 or to wind the steel belt 221 around the bobbin 220.

Specifically, the driving motor 230 may be configured to rotate a driving axis 261a through a bevel gear 264, 264a, wherein such rotation of the driving axis 261a may be transmitted to a timing gear 263 through a plurality of idle gears 262. Furthermore, the timing gear 263 may be connected to an intermittent gear 265 that contacts the steel belt 221 in the housing 200 to rotate the intermittent gear 265, whereby the steel belt 221 may be unwound from the bobbin 220 and be provided towards the probe feeding unit 400.

Meanwhile, the steel belt 221 may be made of an elastic steel such that it may be wound around the bobbin 220 and that it may also transmit the driving force for moving towards the probe feeding unit 400, the steel belt 221 having a roughly half-moon or eyebrow-shaped cross-section. In order words, the steel belt 221 may be formed to have a cross-section of a gently curved arc shape having a predetermined curvature, and thus when unwound from the bobbin 220, the steel belt 221 may be unwound in a straight line manner by the curved cross-section, and be moved along the length direction having a straightness of a predetermined extent, thereby being capable of transmitting the driving force to the probe feeding unit 400. Furthermore, in the steel belt 221, punching holes 221a may be formed along the length direction such that they are distanced by a predetermined distance from one another. These punching holes 221a are for moving the steel belt by the intermittent gear 265 or for unwinding the steel belt, with a securing bump (not illustrated) of the intermittent gear 265 secured to the punching hole 221a, thereby allowing the steel belt 221 to move in an interlocked manner as the intermittent gear is rotated.

Meanwhile, the rail driving unit 200 may have a roller set 270 configured to guide the steel belt 221 being unwound from the bobbin 220 or being wound around the bobbin 220. There may be two roller sets 270 each placed on both sides having the steel belt 221 therebetween, or there may be a plurality of rollers 271 arranged on a curved area where the steel belt 221 is unwound from the rail driving unit 200. The roller set 270 guides the changing of shape of the steel belt 221 during unwinding or winding (that is, changing of shape from a roll shape to a straight shape and vice versa).

Furthermore, the rail driving unit 200 may have a handle unit 240 for manually manipulating the unwinding of the steel belt 221. The handle unit 240 may be arranged in a left cover 213 of the rail driving unit 200, and may consist of a disc-shaped rotating plate 241 having a key hole 241a at its center and mounted to the cover 213 in a rotatable manner, and a handle bar 242 mounted at one side of a circumference of the rotating plate 241 such that it may be gripped by a user. The key hole 241a at the center of the rotating plate 241 may be secured to a driving axis 261a of the gear set 260, and a rotation of the rotating plate 241 may be transmitted to the driving axis 261a through the key hole 241a. That is, when the rotating plate 241 is rotated by the user, the driving axis 261a may be rotated in an interlocked manner with the rotating plate 241, and such a rotation of the driving axis 261a may be transmitted to the intermittent gear 265 through the gear set 260 in a similar manner as the aforementioned driving motor 230, allowing the steel belt 221 to be unwound from the bobbin 220 or to be wound around the bobbin 220. Therefore, the user may be directly adjust unwinding of the steel belt 221 manually when necessary.

Meanwhile, the rail driving unit 200 may have an air supply nozzle 211 where air is supplied and an air discharge nozzle 212 where the supplied air is discharged. The air supply nozzle 211 and air discharge nozzle 212 may each be arranged at one side of the housing, and may provided with a driving air necessary to fix the guide rail 300 that will be explained hereinafter and supply the driving air to the guide rail 300. That is, to the air supply nozzle 211, an air supply means such as an air compressor may be connected. The air supplied may flow inside the housing and be discharged through the air discharge nozzle 212. Herein, the air discharge nozzle 212 is connected to the air supply hole 30 of the guide rail 300 that will be explained hereinafter so that the discharged air may be transferred along the guide rail 300, and the transferred air may be used to drive a fixing piston unit 320 of the guide rail 300 so that the guide rail 300 may be fixed to and supported inside the steam generator. Meanwhile, when necessary, the rail driving unit 200 may also have an air valve 211a for controlling supply and discharge of air.

Furthermore, the rail driving unit 200 may have a horizontal sensor 250 arranged at one side of the housing 200. The horizontal sensor 250 has one or more horizontal meters 251, 253 arranged along a width direction or length direction, and enables an operator to check a state of installation or posture of the rail driving unit 200.

Figure 11:
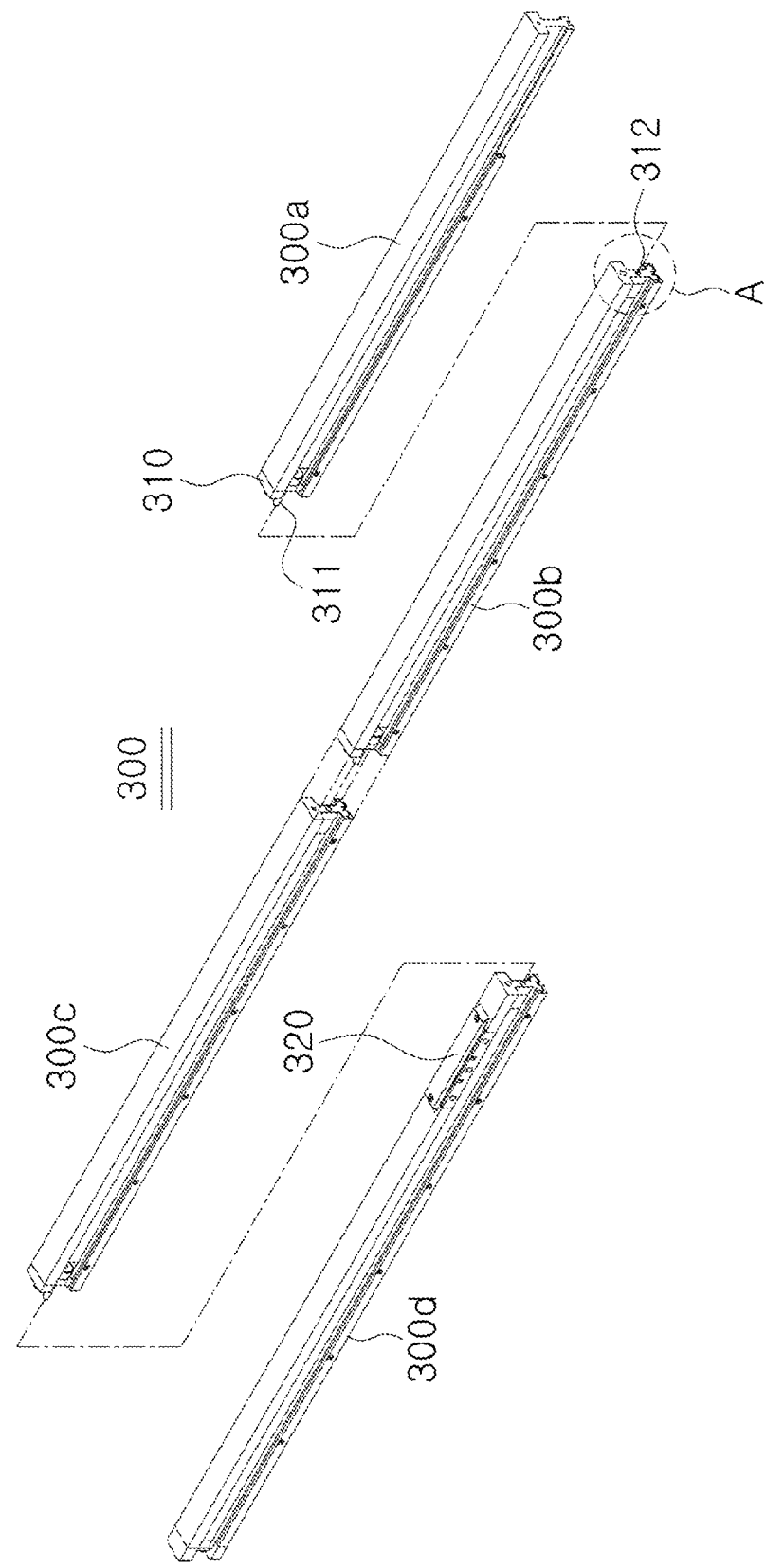
FIG. 11 is an enlarged perspective view of the guide rail illustrated in FIG. 3.
Figure 12:
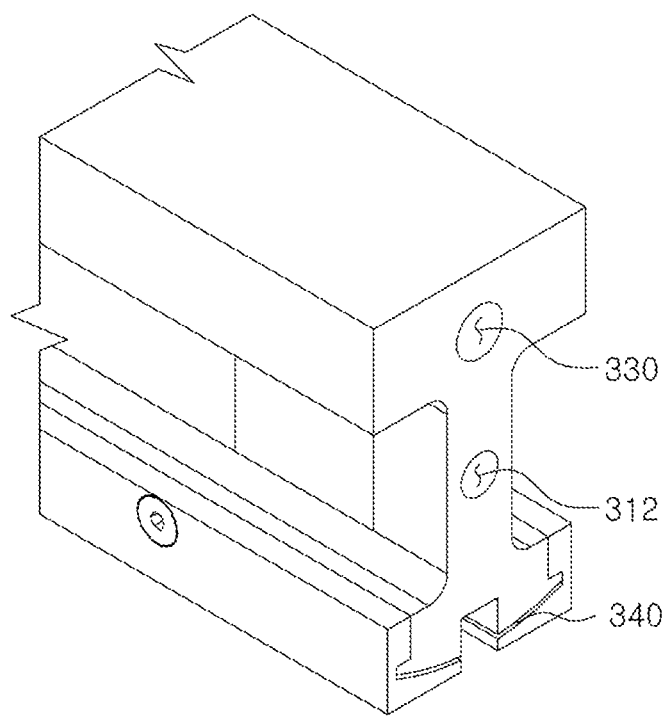
FIG. 12 is an enlarged view of portion A shown in FIG. 11.
Figure 13:
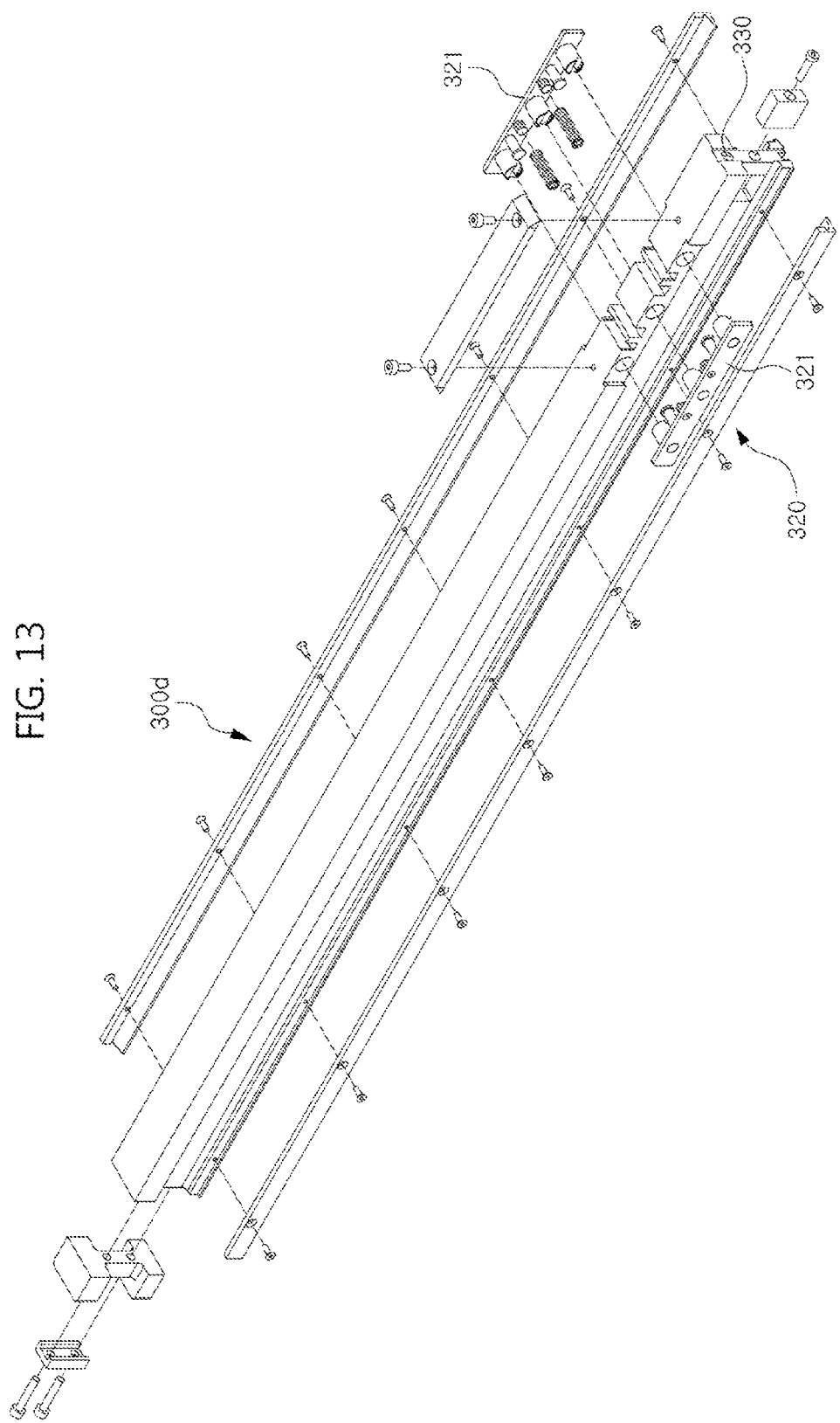
FIG. 13 is an exploded perspective view of a fourth guide rail illustrated in FIG. 11.

FIG. 11 is an enlarged perspective view of the guide rail illustrated in FIG. 3. FIG. 12 is an enlarged view of portion A shown in FIG. 11. FIG. 13 is an exploded perspective view of a fourth guide rail illustrated in FIG. 11.

Referring to FIGS. 11 to 13, the guide rail 300 may have a roughly 'I' shaped cross-section and extend in the length direction. Furthermore, as aforementioned, there may be a plurality of guide rails 300 separately formed. The present embodiment exemplifies a case where a total of four guide rails 300a, 300b, 300c, and 300d are separately formed. Hereinafter, each of the separated guide rails 300a, 300b, 300c, and 300d will be referred to as a first to fourth guide rail 300a, 300b, 300c, and 300d for convenience of explanation.

Figure 2:
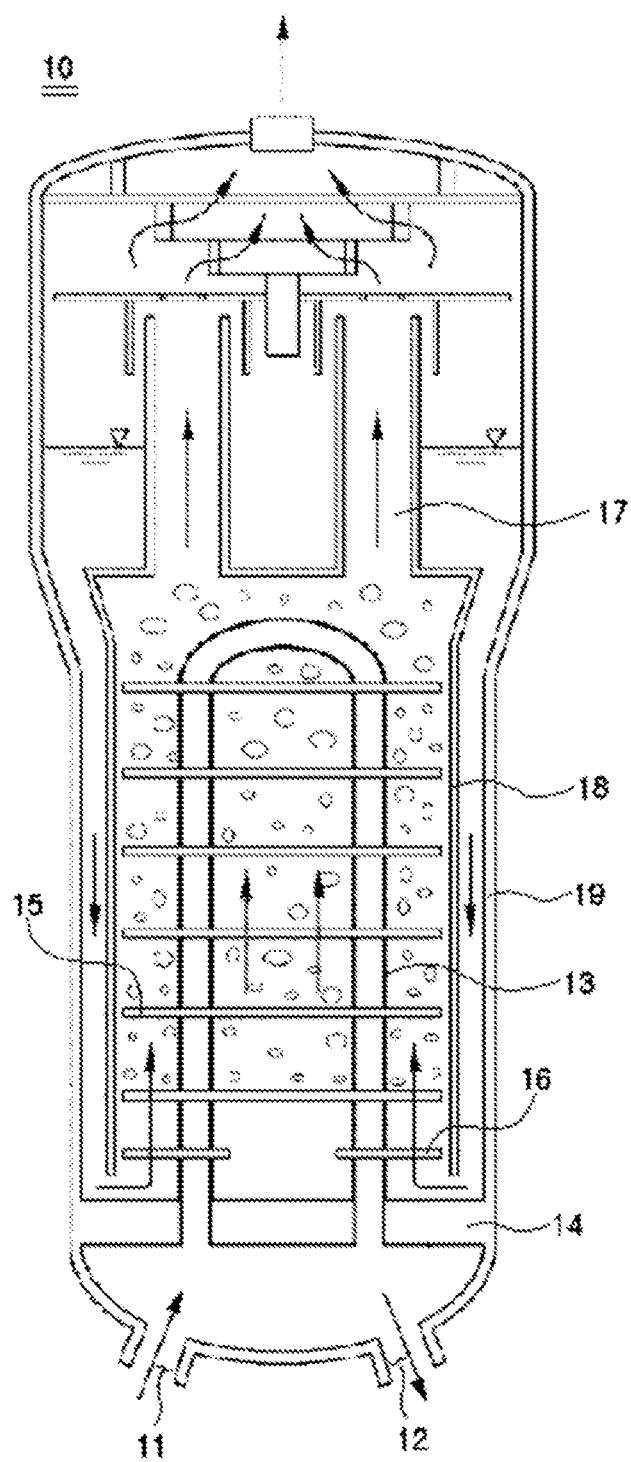
FIG. 2 is a schematic view illustrating an operational principle of a steam generator.

The first guide rail 300a may be provided with a rail driving unit 200 fitted at one end (right end of FIG. 2i) thereof, and the second to fourth guide rails 300b, 300c, and 300d may be connected successively to one another along the length direction of the first guide rail 300a. Herein, at one end of each of the guide rails 300a, 300b, 300c, and 300d, a connecting block 310 may be provided, while at another end thereof, a bolt hole 312 for securing the connecting block 310 may be provided. The connecting block 310 has a connecting bolt 311 configured to be secured to the bolt hole 312, and allows each guide rail 300a, 300b, 300c, and 300d to be connected in the length direction. The connecting block 310 may be made of a substance with a high hardness so that it is not worn out by repeated assembly operations.

Furthermore, the fixing piston unit 320 may be provided in the fourth guide rail 300. The fixing piston unit 320 allows the guide rail 300 inserted inside the steam generator to be fixed to and supported between the heating tubes and divider plate inside the steam generator, and the fixing piston unit 320 may have a pair of pistons 321 configured to be driven by air. The one pair of pistons 321 may each proceed towards the left and right side of the fourth guide rail 300, respectively, by a supply of air, and may each contact the heating tubs and divider plate so that the guide rail 300 extending in the length direction does not sag downwards and be fixed to and supported inside the steam generator.

Meanwhile, such a fixing piston unit 320 may be driven by the air supplied along the guide rail 300, and for this purpose, an air supply hole 330 may be provided such that it penetrates along the length direction. The air supply hole 330 may extend from the first guide rail 300 to which the rail driving unit 200 is fitted to the fourth guide rail 300 where the fixing piston unit 320 is provided, and may be connected to the air discharge nozzle 212 of the rail driving unit 200 so that the air supplied to the air supply nozzle 211 may be transmitted to the fixing piston unit 320.

Furthermore, at a lower end of the guide rail 300, a belt transferring passage 340 for transferring the steel belt 221 may be provided. The belt transferring passage 340 may have a circular arc shape that corresponds to the cross-section of the steel belt 221 and extend along the length direction of the guide rail 300, and the steel belt 221 may be transferred from the rail driving unit 200 to the probe feeding unit 400 through such a belt transferring passage 340. In other words, the steel belt 221 unwound from the bobbin 220 of the rail driving unit 200 may be transferred in the length direction with it inserted into the belt transferring passage 340 formed in the lower end of the guide rail 300, which may cause the probe feeding unit 400 connected to an end of the steel belt 221 to move along the guide rail 300. This will be explained in further detail with relation to the probe feeding unit 400.

Figure 14:
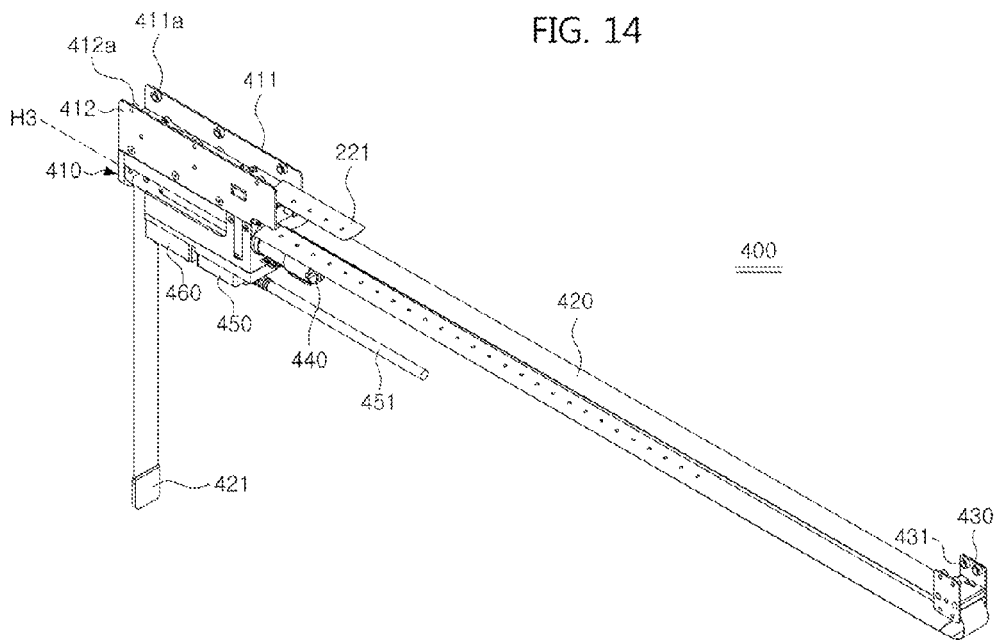
FIG. 14 is an enlarged perspective view of the probe feeding unit illustrated in FIG. 3.
Figure 15:
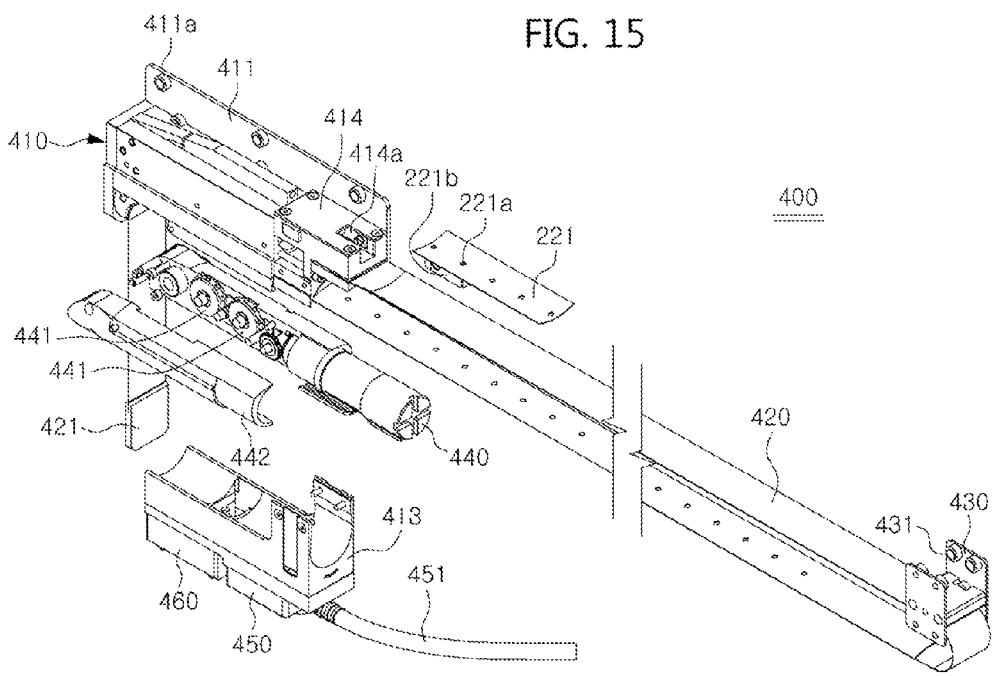
FIG. 15 is a first exploded perspective view of the probe feeding unit illustrated in FIG. 14.
Figure 16:
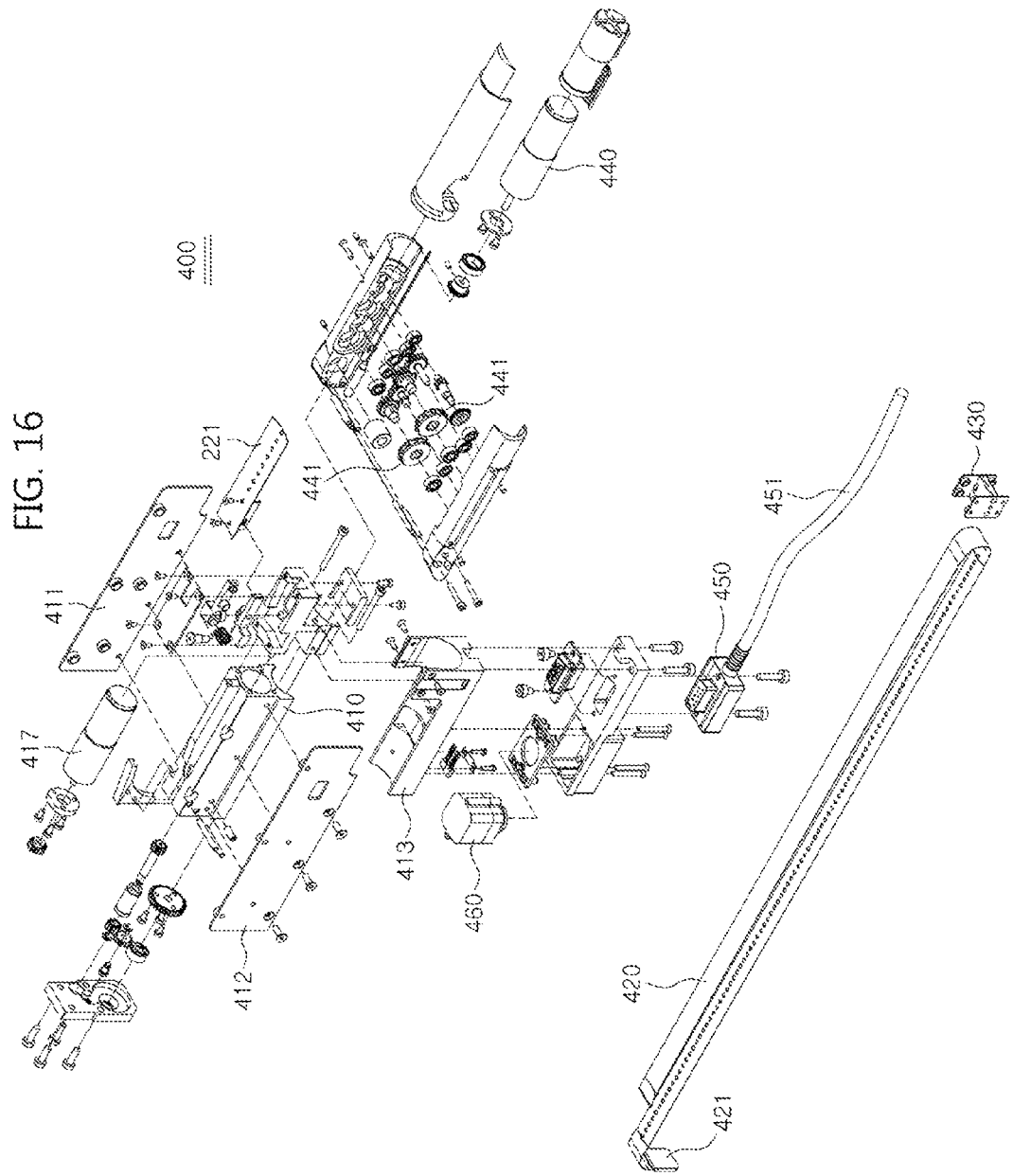
FIG. 16 is a second exploded perspective view of the probe feeding unit illustrated in FIG. 14.

FIG. 14 is an enlarged perspective view of the probe feeding unit illustrated in FIG. 3. FIG. 15 is a first exploded perspective view of the probe feeding unit illustrated in FIG. 14. FIG. 16 is a second exploded perspective view of the probe feeding unit illustrated in FIG. 14.

Referring to FIGS. 14 to 16, the probe feeding unit 400 may have a housing 410. The housing 410 may form a basic frame of the probe feeding unit 400, and may be installed in the aforementioned lower end of the guide rail 300 and be moved along the guide rail 300.

Specifically, the housing 410 may have a pair of roller plates 411, 412 arranged such that they are distanced from each other towards the left and right side, and such a roller plate 411, 412 may have a plurality of rollers 411a, 412a arranged on an inner surface facing each other along a length direction such that they are distanced from one another. Such a roller 411a, 412a may be shoulder-attached to the lower end of the 'I' shaped guide rail 300, and thus the probe feeding unit 400 may be supported by the guide rail 300. The roller 411a, 412a may also conduct a rolling motion above the guide rail 300 so that the probe feeding unit 400 is moved along the length direction of the guide rail 300.

Meanwhile, at one side of the housing 410, a belt securing block 414 for attaching the steel belt 221 may be provided.

The belt securing block 414 may be secured to an end of the steel belt 221 transferred through the belt transferring passage 340 of the guide rail 300 from the rail driving unit 200, whereby the probe feeding unit 400 is moved along the guide rail 300 as the steel belt 221 is transferred along the length direction. When necessary, for a fast attachment or release between the belt securing block 414 and steel belt 221, at a lower surface of the end of the steel belt 221, a dog 221b having a securing groove (not illustrated) may be provided, and in the belt securing block 414, a belt assembly groove 414a where such a dog 221b may be inserted and fixed may be provided. In the belt assembly groove 414a, a securing bump (not illustrated) may be provided such that it is elastically supported by a spring and so forth and that interlocks with the securing groove.

Meanwhile, the probe feeding unit 400 may be provided with a probe 420 configured to be inserted into a gap between the heating tubes to inspect foreign substance or sludge and so forth in an exterior or interior of the heating tubes. The probe 420 may be formed to have a shape of a band extending along a length direction, and may be curved in a 'U' shape as it passes a trolley 430 that will be explained hereinafter, and then extending towards a lower side of the housing 410 again. The probe 420 may be configured to have a structure similar to the aforementioned steel belt 221, the probe 420 having a cross-section of a roughly circular arc shape extending in the length direction, and a plurality of punching holes (not illustrated) formed along the length direction such that they are distanced from one another.

Furthermore, the probe 420 may extend along the length direction towards the trolley 430 at a rear side with one end of the probe 420 fixed to and installed in the housing 410, and may be curved in a 'U' shape as it passes the trolley 430, and then extending towards the housing 410 again. The probe 420 extending towards the housing 410 may be bent by about 90 degrees downwards and thus extend towards the lower side of the housing 410, and at an end of the probe 420 extending towards the lower side of the housing 410, an inspection camera 421 may be mounted. Such a probe 420 may be made of an elastic substance such as metal and have a cross-section of a circular arc shape similarly as the aforementioned steel belt 221, and may thus be curved or bent by a predetermined extent, but when unwound in a straight line, the probe 420 may maintain the straight line format while having a hardness of a predetermined extent. However, a soft thin film circuit may be adhered to an exterior of the probe 420 at a high temperature and high pressure so that it may transmit an image signal from the inspection camera 421.

Meanwhile, the probe feeding unit 400 may have a trolley 430 configured to support one side of the probe 420 and distanced from the housing 410. The trolley 430 may have a plurality of rollers shoulder-attached to a lower end of the guide rail 300 and configured to conduct a rolling motion to move along the guide rail 300. Such a movement of the trolley 430 is made by a drive of a motor 440 that will be explained hereinafter, and as the trolley 430 moves along the guide rail 300, a length of the probe 420 being unwound to a lower end of the housing 410 is adjusted. In other words, when the trolley 430 is moved towards the housing 410, the probe 420 may be further unwound to the lower end of the housing, whereas when the trolley 430 is moved to be distanced from the housing 410, the length of the probe 420 unwound to the lower end of the housing 410 becomes shorter. This will be explained in more detail with respect to the feeding motor 440 that will be explained hereinafter.

The probe feeding unit 400 may have a feeding motor 440 configured to transfer the probe in a length direction to adjust a length of the probe 420 being unwound. The feeding motor 440 may be mounted onto and accommodated in a motor casing 442 arranged in a lower side of the housing 410, and may be connected to the intermittent gear 441 through the bevel gear and so forth arranged inside the motor casing 442 to drive the intermittent in a rotatable manner. Furthermore, the intermittent gear 441 may have a securing bump (not illustrated) configured to interlock with the punch hole formed in the probe 420, and when driven in a rotatable manner, the intermittent gear 441 may transfer the probe 420 in a length direction. The probe 420 may be arranged between the housing 410 and motor casing 442 and may be transferred along the length direction by the intermittent gear 441, and may be bent by 90 degrees by a guider (not illustrated) of an end (left end of FIG. 5) of the motor casing 442, and be unwound towards below the motor casing 442.

Meanwhile, the probe feeding unit 400 may have a twisting motor 470 connected to the motor casing 442 and configured to rotate the probe 420 unwound towards below the motor casing 442 around a third hinge axis (H3) having a length direction. The twisting motor 470 may be connected to the motor casing 442 through a gear and so forth, and may rotate the motor casing 442 around the third hinge axis H3 having a length direction by a predetermined extent. That is, the motor casing 442 may be rotated around the third hinge axis H3 with respect to the housing 410 by a predetermined extent, and by such rotation of the motor casing 442, the probe 420 unwound towards below the motor casing 442 may be rotated around the third hinge axis H3 by a predetermined extent. In this case, in the probe 420 extending in the length direction, a twist of a predetermined extent may occur, and by the rotation of the probe 420, the camera 421 and so forth may be moved towards the gap between the heating tubes.

Furthermore, the probe feeding unit 400 may have a cable connector 450 and monitoring camera 360 to which a cable for power supply and drive control is connected. Such a cable connector 450 and monitoring camera 460 may be arranged in a lower cover 413 that is assembled in a lower portion of the housing 410. Furthermore, the monitoring camera 460 or the aforementioned inspection camera 421 may have a lighting means. This is a result of considering the fact that since the interior of the steam generator where the probe feeding unit 400 operates is an underwater environment that is completely sealed, a lot of light would be absorbed and thus it would be difficult to identify a subject.

Figure 17:
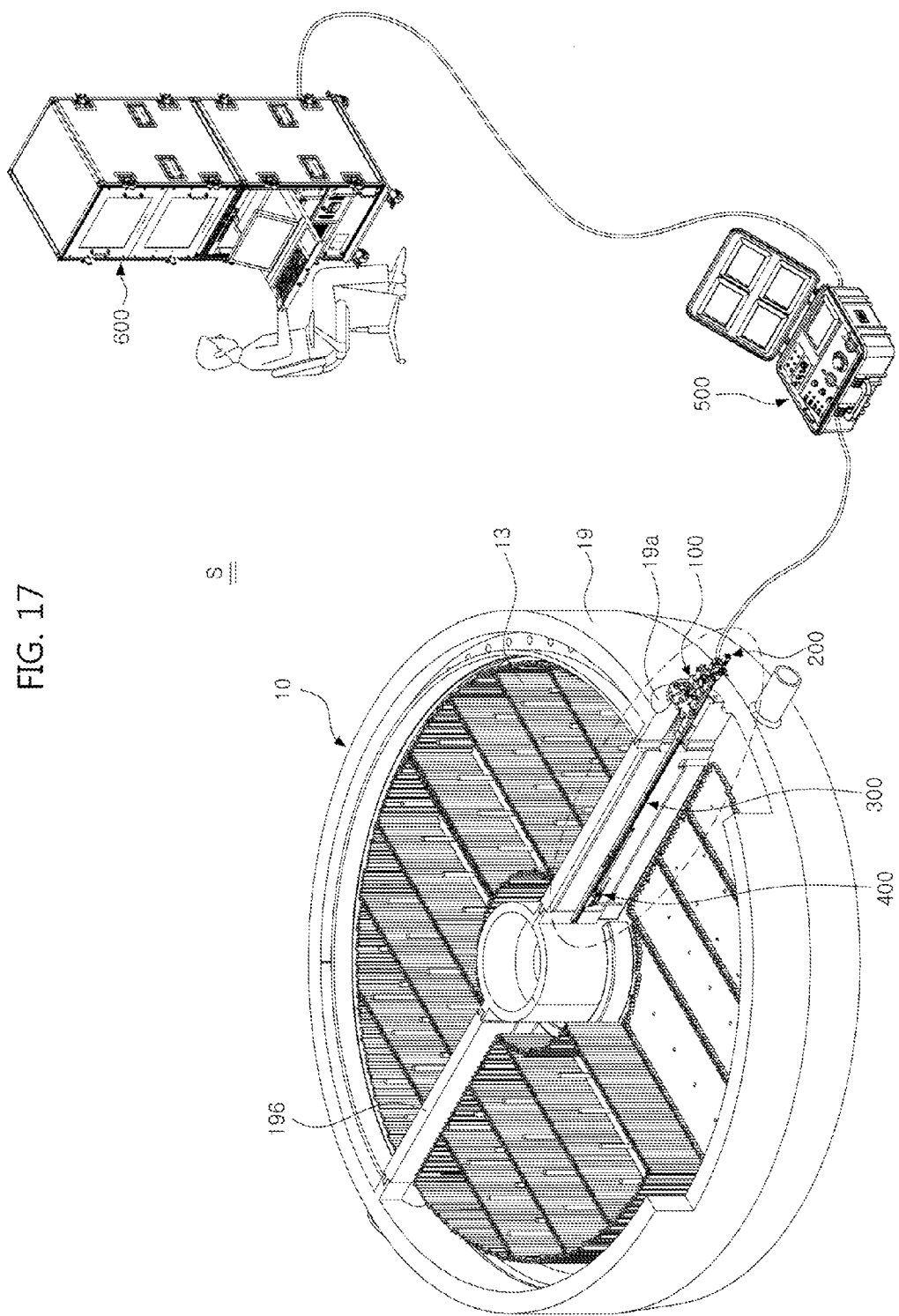
FIG. 17 is a view illustrating an installed state of the remote inspection apparatus for a heating tube of a steam generator illustrated in FIG. 3.
Figure 18:
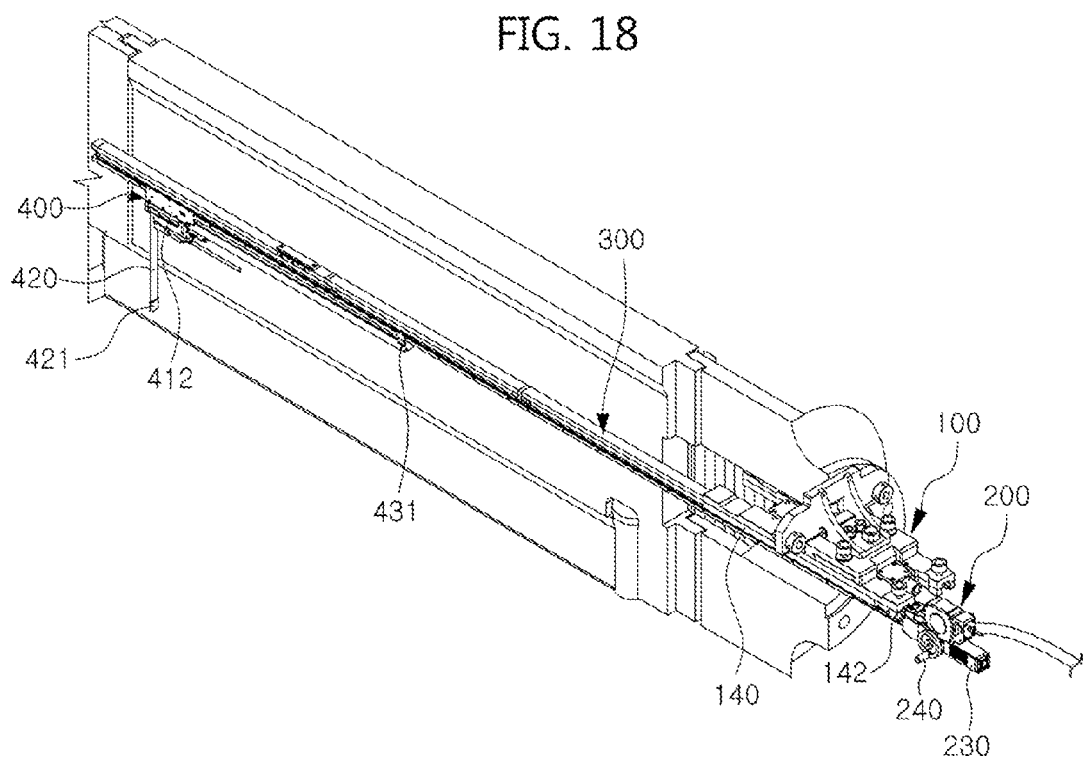
FIG. 18 is a partial enlarged view of FIG. 17.

FIG. 17 is a view illustrating an installed state of the remote inspection apparatus for a heating tube of a steam generator illustrated in FIG. 3; and FIG. 18 is a partial enlarged view of FIG. 17.

FIGS. 17 and 18 illustrate an installed state of the remote inspection apparatus (S) with the main focus on the lower side of the steam generator 10 of portion B shown in FIG. 1.

Referring to FIGS. 17 and 18, how to install and use the remote inspection apparatus (S) according to the embodiment of the present disclosure will be explained hereinafter. First, an operator installs the fixing unit 100 through the hand hole 19a formed in the external casing 19 of the steam generator 10. These hand holes 19a may be formed along a circumference of the steam generator 10 such that they are distanced by approximately 180 degrees from one another. As aforementioned, the fixing block 110 may be installed in a fixed manner as the fixing block 110 is bolt-attached to the flange surface of the hand hole 19a, and the position and posture of the rail guider 140 may be adjusted by the hinge block 120 and sliding block 130 and so forth.

When installing the fixing unit 100 is completed as aforementioned, the operator secures the guide rail 300 to the rail guider 140, and moves the guide rail 300 in the length direction along the rail guider 140 so that it enters the steam generator 10. Herein, the guide rail 300 may enter an empty space between the divider plate 19b and heating tubes inside the steam generator 10, the divider plate 19b indicating a type of partition wall that divides the interior of the steam generator 10 into left and right. Furthermore, in a case where there are a plurality of guide rails 300 separately formed, the operator may repeat inserting and connecting each guide rail 300 successively such that they enter the guide rails 300 up to a position set for inspection.

Meanwhile, when the guide rail 30 enters the steam generator 10, the operator may install the rail driving unit 200 at an end of the guide rail 300 where the fixing unit 100 is arranged, and may also install the probe feeding unit 400 in the guide rail 300 to conduct an inspection. Herein, the rail driving unit 200 may supply driving air to the guide rail 300 through the air supply nozzle 211 and air discharge nozzle 212, and the air supplied may be moved along the air supply hole 330 of the guide rail 300 and be provided to the fixing piston unit 320. Furthermore, the fixing piston unit 320 proceeds the one pair of pistons 321 to the left and right side through the supplied air, and as each piston 321 contacts and is supported by the divider plate 19b and heating tubes 13, the guide rail 300 may be supported inside the steam generator 10 in a fixed manner.

Furthermore, the rail driving unit 200 transfers the steel belt 221 wound around the bobbin 220 in the length direction, and the steel belt 221 is transferred along the belt transferring passage 340 of the guide rail 300 to move the probe feeding unit 400 fitted to an end. Such transferring of the steel belt 221 made in the length direction may be made automatically by the driving motor 230 provided in the rail driving unit 200, or manually as the operator directly manipulates the handle unit 240.

When the probe feeding unit 400 is moved along the guide rail 300 and is arranged in a position set for inspection, the operator inserts the probe 420 into the gap between the heating tubes 13 through the local control unit 500 outside the steam generator 10 or the remote control unit 600 outside the reactor. That is, by controlling the feeding motor 440 to adjust the length of the probe 420, and rotating the probe 420 through the twisting motor 417, the probe 420 and the inspection camera 421 fitted to an end of the probe 420 are inserted into the gap between the heating tubes 13, and as an image signal photographed by the inspection camera 421 is transmitted to the remote control unit 600 and so forth, the operator is enabled to check in real time whether or not there is foreign substance or sludge deposited in the gaps between the heating tubes.

As aforementioned, a remote inspection apparatus for a heating tube of a steam generator according to various embodiments of the present disclosure may be easily installed through a hand hole of the steam generator, may easily approach even an area where a conventional inspection apparatus could not have easily reached, and may thus contribute to thoroughly inspecting the steam generator or heating tubes and securing integrity thereof.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

REFERENCE NUMERALS

S: REMOTE INSPECTION APPARATUS FOR A HEATING TUBE OF A STEAM GENERATOR

| | |
|---|---|
| 100: FIXING UNIT | 110: FIXING BLOCK |
| 120: HINGE BLOCK | 130: SLIDING BLOCK |
| 140: RAIL GUIDER | 200: RAIL DRIVING UNIT |
| 210: HOUSING | 220: BOBBIN |
| 230: DRIVING MOTOR | 240: HANDLE UNIT |
| 250: HORIZONTAL SENSOR | 260: GEAR SET |
| 270: ROLLER SET | 300: GUIDE RAIL |
| 310: CONNECTING BLOCK | 320: FIXING PISTON UNIT |
| 330: AIR SUPPLY HOLE | 340: BELT TRANSFERRING PASSAGE |
| 400: PROBE FEEDING UNIT | 410: HOUSING |
| 420: PROBE | 430: TROLLEY |
| 440: FEEDING MOTOR | 450: CABLE CONNECTOR |
| 460: MONITORING CAMERA | 470: TWISTING MOTOR |
| 500: LOCAL CONTROL UNIT | 600: REMOTE CONTROL UNIT |

What is claimed is:

1. A remote inspection apparatus for a heating tube of a steam generator, the apparatus comprising:
   a fixing unit 100 installed in a flange surface of a hand hole 19a of the steam generator 10 in a fixed manner, and having one or more rail guiders 140 for guiding a guide rail 300 into the steam generator 10;
   the guide rail 300 configured to be guided by the rail guider 140 to enter between the heating tube 13 and a divider plate 19a inside the steam generator;
   a rail driving unit 200 fitted at one end of the guide rail 300 and arranged outside the steam generator 10, and having a bobbin 220 around which a steel belt 221 is wound; and
   a probe feeding unit 400 configured to receive a driving force from the rail driving unit 200 through the steel belt 221 to be moved along the guide rail 300, and having a band shaped probe 420 extending in a length direction and an inspection camera 421 fitted at one end of the probe 420 wherein the fixing unit 100 comprises a fixing block 110 configured to be bolt-attached to the flange surface of the hand hole 19a through a fixing bolt 111; a hinge block 120 secured to the fixing block 110 such that it is rotatable by a predetermined extent around a first hinge axis (H1) having an up-down direction; and a sliding block 130 secured to the hinge block 120 such that it is rotatable by a predetermined extent around a second hinge axis (H2) having a width direction, and having the rail guider 140 fitted to and supported by a lower surface of the sliding block 130; wherein the sliding block 130 is provided with a sliding groove 131 having a reversed trapezoidal shape extending in a width direction on a lower surface of the sliding block 130, and the rail guider 140 comprises a mounting block 141 having a shape corresponding to the sliding groove 131 on an upper surface of the rail guider 140, and is configured such that it is movable in a sliding manner in a width direction with respect to the sliding block 130.

2. The apparatus according to claim 1,
wherein there are a plurality of rail guiders 140, each rail guider 140 having a rail guiding groove 142 extending in a length direction on a lower surface of the rail guider 140 for the guide rail 300 to be inserted and secured, and
the plurality of rail guiders 140 are distanced from one another in a width direction.

3. The apparatus according to claim 1,
wherein there are a plurality of guide rails 300 separately formed along a length direction.

4. The apparatus according to claim 1,
wherein the guide rail 300 comprises a belt transferring passage 340 along a length direction, and
the steel belt 221 is supplied to the probe feeding unit 400 as it is accommodated in the belt transferring passage 340 and transferred in a length direction.

5. The apparatus according to claim 1,
wherein the guide rail 300 comprises a fixing piston unit 320 at one side of the guide rail 300,
the fixing piston unit 320 having a pair of pistons 321 each configured to be driven by air and be proceeded in a width direction to contact and be supported by the heating tube 13 or divider plate 19b, and
the guide rail 300 has an air supply hole 330 along a length direction to supply air needed to drive each piston 321 from the rail driving unit 200 to the fixing piston unit 320.

6. The apparatus according to claim 1,
wherein the rail driving unit 200 comprises a housing 210 for accommodating and supporting the bobbin 220 inside the housing 210;
an intermittent gear 265 interlocked with a punching hole 221a of the steel belt 221 to wind or unwind the steel belt 221 from or around the bobbin 220; and
a driving motor 230 connected to the intermittent gear 265 to provide a driving force.

7. The apparatus according to claim 6,
wherein the rail driving unit 200 comprises a handle unit 240 configured to manually rotate the intermittent gear 265,
the handle unit 240 comprising a rotating plate 241 having a key hole 241a at its center, and secured to a driving axis 261a connected to the intermittent gear 265; and
a handle bar 242 provided at one side of the rotating plate 241 to provide a gripping point for a user.

8. The apparatus according to claim 6,
wherein the rail driving unit 200 comprises a horizontal sensor 250 having one or more horizontal meters 251, 252, and configured to be fitted to one side of the housing 210;
an air supply nozzle 211 fitted to one side of the housing 210 to be connected to an air supply means; and
an air discharge nozzle 212 connected to the guide rail 300 to supply air to the guide rail 300.

9. The apparatus according to claim 6,
wherein the steel belt 221 has an arc shaped cross-section with a predetermined curvature extending in a length direction, and is provided with a plurality of punching holes 221a distanced from one another by a predetermined distance along the length direction.

10. The apparatus according to claim 1,
wherein the probe feeding unit 400 comprises a housing having a plurality of rollers 411a, 412b shoulder-attached to the guide rail 300 at its top end to conduct a rolling motion on top of the guide rail 300, and secured to an end of the steel belt 221 to be moved along a length direction of the guide rail 300;
a trolley 430 distanced from the housing 410 by a predetermined distance, and configured to support one side of the probe 420 and to be moved along the guide rail 300; and
a feeding motor 440 connected to an intermittent gear 441 configured to transfer the probe 420 in a length direction to wind or unwind the probe 420.

11. The apparatus according to claim 10,
wherein the probe 420 is arranged such that an opposite side of an end to which the inspection camera 421 is fitted is installed in the housing 410 in a fixed manner so that the probe 420 may extend towards the trolley 430, that it is curved in a 'U' shape by the trolley 430 to extend towards the housing 410 again, and that it is curved perpendicularly downwards to extend to a lower side of the housing 410.

12. The apparatus according to claim 11,
wherein the feeding motor 440 adjusts a length of the probe 420 transferred in a length direction and extending towards the lower side of the housing, and
the trolley 430 is moved along the guide rail 300 as the probe 420 is transferred in the length direction.

13. The apparatus according to claim 10,
wherein the probe 420 has an arc shaped cross-section with a predetermined curvature extending in a length direction, and is provided with a plurality of punching holes 221a interlocked with the intermittent gear 441 and distanced from one another by a predetermined distance along the length direction.

14. The apparatus according to claim 10,
wherein the probe feeding unit 400 comprises a belt securing block 414 having a belt assembly groove 414a configured to be secured to a dog 221b provided at an end of the steel belt 221;
a monitoring camera 460 arranged at a lower side of the housing 410; and
a cable connector 450 to which a cable 451 for drive control or power supply is connected.

* * * * *